(12) United States Patent  
Mikami et al.

(10) Patent No.: US 7,756,246 B2  
(45) Date of Patent: Jul. 13, 2010

(54) MEDICAL IMAGING APPARATUS

(75) Inventors: Yuji Mikami, Kaisei-machi (JP); Tomonari Sendai, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/453,541

(22) Filed: May 14, 2009

(65) Prior Publication Data  
US 2009/0290679 A1 Nov. 26, 2009

(30) Foreign Application Priority Data  
May 21, 2008 (JP) .............................. 2008-132757

(51) Int. Cl.  
A61B 6/04 (2006.01)
(52) U.S. Cl. ....................................................... 378/37
(58) Field of Classification Search .................... 378/4, 378/19, 20, 37, 62, 70, 86–90  
See application file for complete search history.

(56) References Cited  
U.S. PATENT DOCUMENTS  
4,905,269 A * 2/1990 Mosby ........................ 378/182

2002/0173722 A1 * 11/2002 Hoctor et al. ................ 600/443

FOREIGN PATENT DOCUMENTS  
JP 3461509 8/2003  
WO WO 95/11627 5/1995

* cited by examiner

*Primary Examiner*—Irakli Kiknadze  
(74) *Attorney, Agent, or Firm*—Jean C. Edwards, Esq.; Akerman Senterfitt

(57) ABSTRACT

The time for obtaining ultrasonic images can be reduced by using a two-dimensional transducer array and good radiation images can be obtained even when radiation imaging is performed with the fixed array. The medical imaging apparatus includes a radiation generating unit for generation radiation, a radiation detecting unit for detecting radiation, an ultrasonic transducer array provided between the radiation generating unit and the radiation detecting unit and including two-dimensionally arranged ultrasonic transducers, a radiation image data generating unit for generating radiation image data based on a detection result of the radiation detecting unit, and an image processing unit for performing image processing on the radiation image data generated based on a detection result of radiation transmitted through an object to be inspected and the ultrasonic transducer array, thereby removing an image of the ultrasonic transducer array from a radiation image represented by the radiation image data.

8 Claims, 8 Drawing Sheets

6 ULTRASONIC TRANSDUCERS

MEDICAL IMAGING APPARATUS

CROSS-REFERENCE TO RELATED APPLICATIONS

The present application claims priority from Japanese Patent Application No. 2008-132757, filed May 21, 2008, the contents of which are herein incorporated by reference in their entirety.

BACKGROUND OF THE INVENTION

1. Field of the Invention

The present invention relates to a medical imaging apparatus for imaging mammary gland and breast by using radiation and ultrasonic waves for diagnoses of breast cancer.

2. Description of a Related Art

Conventionally, an imaging method using radiation (X-ray, α-ray, β-ray, γ-ray, electron ray, ultraviolet ray, or the like) is utilized in various fields, and particularly, in the medical field, the method is one of the most important means for diagnoses. Radiation images obtained by X-ray imaging (X-ray mammography) of breasts for breast cancer diagnoses are useful for finding calcification as a precursor of mass and cancer, but finding calcification may be difficult depending on mammary gland density or the like of an object to be inspected. Accordingly, it has been studied to use radiation and ultrasonic waves in combination to make diagnoses based on both radiation images and ultrasonic images. X-ray mammography and ultrasonic imaging have the following features, respectively.

X-ray mammography is suitable for exposing calcification as one of early symptoms of a cancer, and enables detection with high sensitivity and high resolving power. Especially, in the case where mammary gland tissues have become atrophied and replaced with fat (so-called "fat breast") as is the case of postmenopausal women, more information can be obtained by X-ray mammography. However, the X-ray imaging has a disadvantage that detection capability of specific natures of tissues (tissue properties) is low.

Further, in an X-ray image, mammary glands are expressed in homogeneous soft tissue density, and thus, the detection of tumor mass is difficult for the case where mammary glands have developed (so-called, "dense breast") as is the case of adolescent to premenopausal women. Furthermore, in X-ray mammography, only two-dimensional images can be obtained in which an object to be inspected as a solid is projected on a plane. On this account, even when a tumor mass is found, it is difficult to grasp information on the location in the depth direction, size, and so on of the tumor mass.

On the other hand, in ultrasonic imaging, specific natures of tissues (e.g., the difference between a cystic tumor and a solid matter) can be detected and also a lobular cancer can be detected. Further, real time observation of images and three-dimensional image generation are possible. However, accuracy of ultrasonic imaging examination often depends on the skill of an operator such as a doctor, and reproducibility is low. Further, it is difficult to observe minute calcification in an ultrasonic image.

As described above, X-ray mammography examination and ultrasonic imaging examination have both merits and demerits, and it is desirable that both examinations are performed for reliably finding breast cancer. Since the X-ray mammography examination is performed while the object (breast) is compressed by a compression plate, in order to make diagnoses based on X-ray images and ultrasonic images of the object in the same condition, the ultrasonic imaging examination is necessary to be performed in the same condition as that when the X-ray mammography examination is performed, that is, while the object (breast) is compressed by the compression plate. For this purpose, a medical imaging apparatus for imaging mammary gland and breast by using radiation and ultrasonic waves in combination is considered.

In the medical imaging apparatus, when the object (breast) compressed by the compression plate is mechanically scanned by using a one-dimensional ultrasonic transducer array, there is a problem that it takes time to obtain an ultrasonic image. Accordingly, in order to reduce the time taken for obtaining an ultrasonic image, it is considered to use a two-dimensional ultrasonic transducer array.

As a related technology, Japanese Patent JP-B-P3461509 (International Publication WO95/011627) discloses an apparatus for imaging breast tissues by using both X-ray and ultrasonic technologies including a two-dimensional ultrasonic transducer array below a grid provided under a compression plate. In this apparatus, connecting wires of the two-dimensional ultrasonic transducer array are provided across the two-dimensional ultrasonic transducer array in alignment with X-ray absorbent material rows of the grid, and the connecting wires form no image on an X-ray film during radiation to the X-ray film.

However, if X-ray imaging is performed with the grid remaining stationary, no image of the connecting wires is formed but an image of the grid is formed. In order not to form the image of the grid, it is necessary to perform X-ray imaging while moving the grid with the two-dimensional ultrasonic transducer array, and the movement mechanism becomes complex in this case.

SUMMARY OF THE INVENTION

The present invention has been achieved in view of the above-mentioned problems. A purpose of the present invention is to provide a medical imaging apparatus in which the time for obtaining ultrasonic images can be reduced by using a two-dimensional transducer array and good radiation images can be obtained even when radiation imaging is performed with the two-dimensional transducer array remaining fixed.

In order to accomplish the above-mentioned purpose, a medical imaging apparatus according to one aspect of the present invention includes: a radiation generating unit for generation radiation; a radiation detecting unit for detecting radiation; an ultrasonic transducer array provided between the radiation generating unit and the radiation detecting unit and including two-dimensionally arranged ultrasonic transducers; a radiation image data generating unit for generating radiation image data based on a detection result of the radiation detecting unit; and an image processing unit for performing image processing on the radiation image data generated based on a detection result of radiation generated by the radiation generating unit and transmitted through an object to be inspected and the ultrasonic transducer array, thereby removing an image of the ultrasonic transducer array from a radiation image represented by the radiation image data.

According to the one aspect of the present invention, the time for obtaining ultrasonic images can be reduced by using a two-dimensional transducer array, and good radiation images can be obtained even when radiation imaging is performed with the two-dimensional transducer array remaining fixed by performing image processing of removing the image of the ultrasonic transducer array from the radiation image generated based on the detection result of the radiation transmitted through the object and the ultrasonic transducer array.

DESCRIPTION OF THE PREFERRED EMBODIMENTS

Hereinafter, preferred embodiments of the present invention will be explained in detail with reference to the drawings. The same reference numbers are assigned to the same component elements and the description thereof will be omitted.

Figure 1:
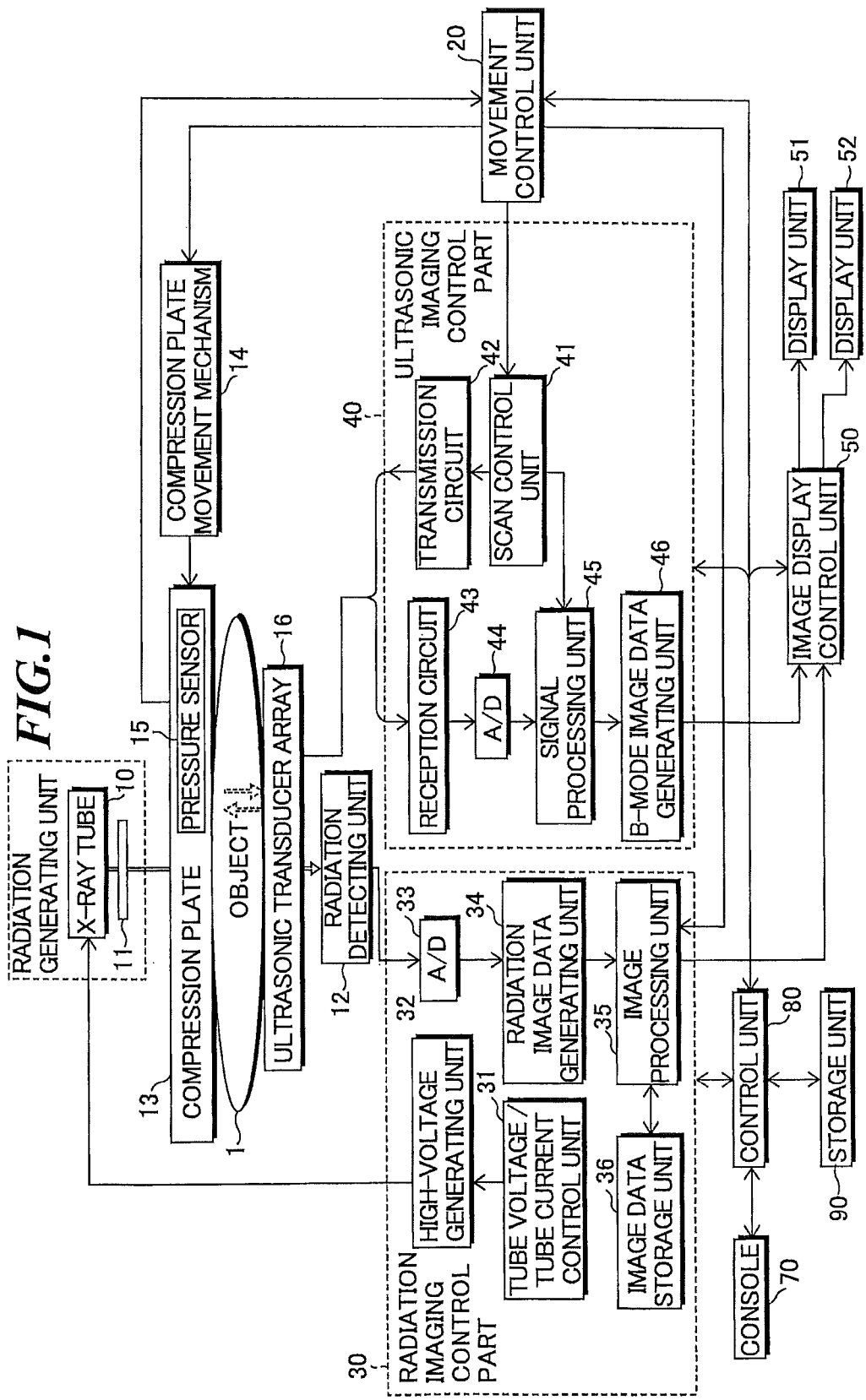
FIG. 1 is a block diagram showing a configuration of a medical imaging apparatus according to the first embodiment of the present invention.

FIG. 1 is a block diagram showing a configuration of a medical imaging apparatus according to the first embodiment of the present invention. The medical imaging apparatus is a medical imaging apparatus having both a function of a radiation mammography apparatus for applying radiation to a breast, detecting the radiation transmitted through the breast, and thereby, generating a radiation image, and a function of an ultrasonic diagnostic apparatus for transmitting ultrasonic waves to the breast, receiving ultrasonic echoes reflected within the breast, and thereby, generating an ultrasonic image. As below, the case of using an X-ray as radiation will be explained, however, α-ray, β-ray, γ-ray, electron ray, ultraviolet ray, or the like may be used.

As shown in FIG. 1, the medical imaging apparatus has an X-ray tube 10 and a filter 11, which form a radiation generating unit, a radiation detecting unit 12 for detecting an X-ray generated by the X-ray tube 10 and transmitted through an object to be inspected 1, a compression plate 13 for pressing a breast as the object, a compression plate movement mechanism 14 for moving the compression plate 13, a pressure sensor 15 for detecting pressure applied to the compression plate 13, and an ultrasonic transducer array 16 including plural ultrasonic transducers for transmitting and receiving ultrasonic waves in an imaging unit.

Further, the medical imaging apparatus has a movement control unit 20 for controlling the compression plate movement mechanism 14 and so on, a radiation imaging control part 30, an ultrasonic imaging control part 40, an image display control unit 50, display units 51 and 52, a console 70, a control unit 80, and a storage unit 90.

Figure 2:
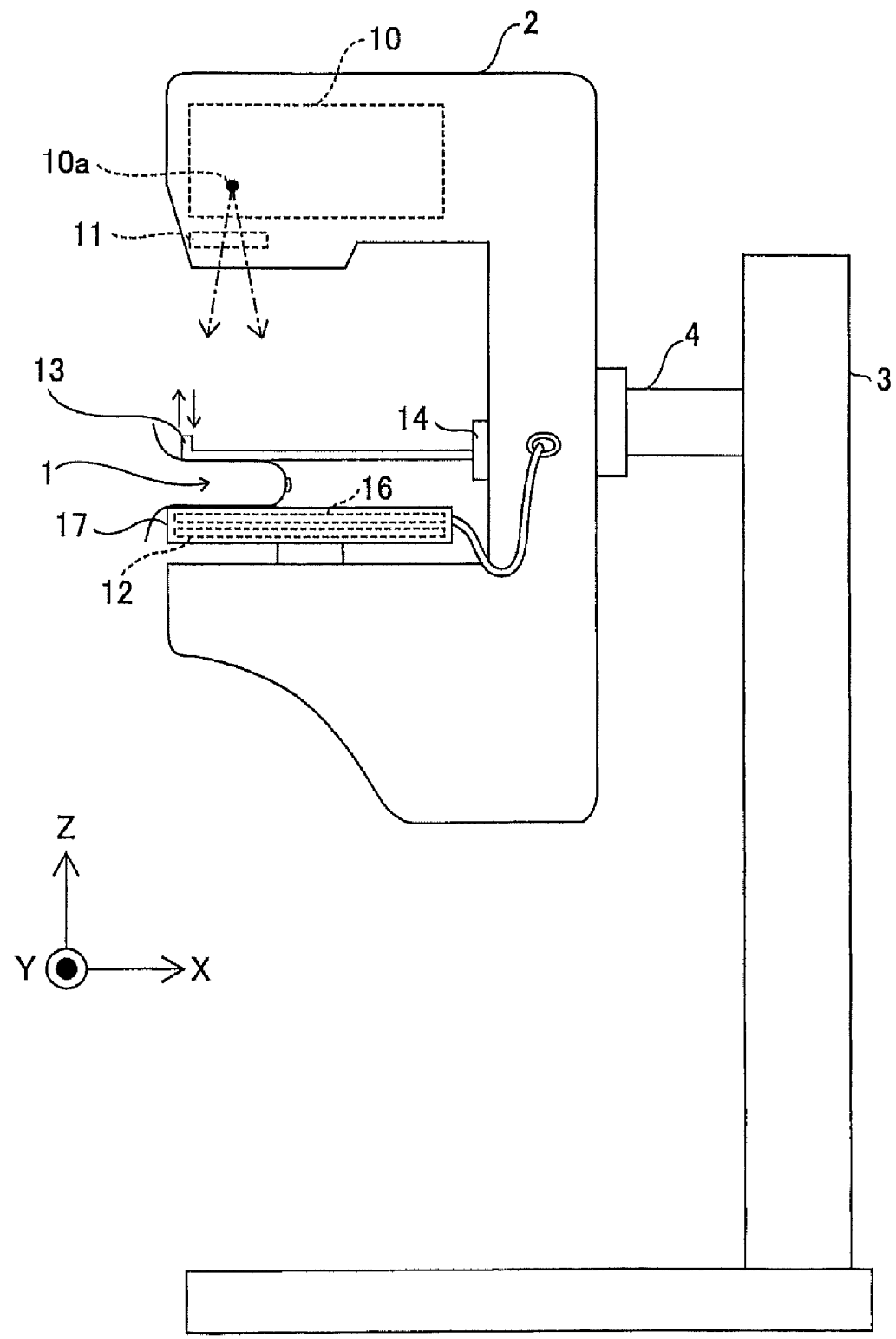
FIG. 2 is a side view showing an appearance of an imaging unit in the medical imaging apparatus according to the first embodiment of the present invention.

FIG. 2 is a side view showing an appearance of the imaging unit in the medical imaging apparatus according to the first embodiment of the present invention. As shown in FIG. 2, the imaging unit of the medical imaging apparatus has an arm part 2, a support 3 for holding the arm part 2 movably in the vertical direction (Z-axis direction), and a shaft part 4 for connecting the arm part 2 to the support 3. The arm part 2 is provided with the X-ray tube 10, the filter 11, an imaging stage 17 on which the object 1 is mounted, the compression plate 13 for pressing the object 1 between the imaging stage 17 and itself, and the compression plate movement mechanism 14 for moving the compression plate 13. The X-ray tube 10 has a focal point 10a inside thereof. Further, the radiation detecting unit 12 and the ultrasonic transducer array 16 are provided within the imaging stage 17.

The compression plate 13 is provided in parallel to the imaging stage 17, and the compression plate movement mechanism 14 moves the compression plate 13 substantially in the vertical direction (Z-axis direction) under the control of the movement control unit 20 (FIG. 1). The pressure sensor 15 (FIG. 1) detects the pressure applied to the compression plate 13 and the movement control unit 20 controls the compression plate movement mechanism 14 based on the detection result. The object (breast) 1 is sandwiched by the compression plate 13 and the imaging stage 17, and X-ray imaging and ultrasonic imaging are performed with the homogeneous thickness of the breast. Here, it is desirable that the compression plate 13 is optically transparent for positioning and confirmation of the compression state when compressing the breast, and formed of a material that transmits the X-ray radiated from the X-ray tube 10.

Figure 3:
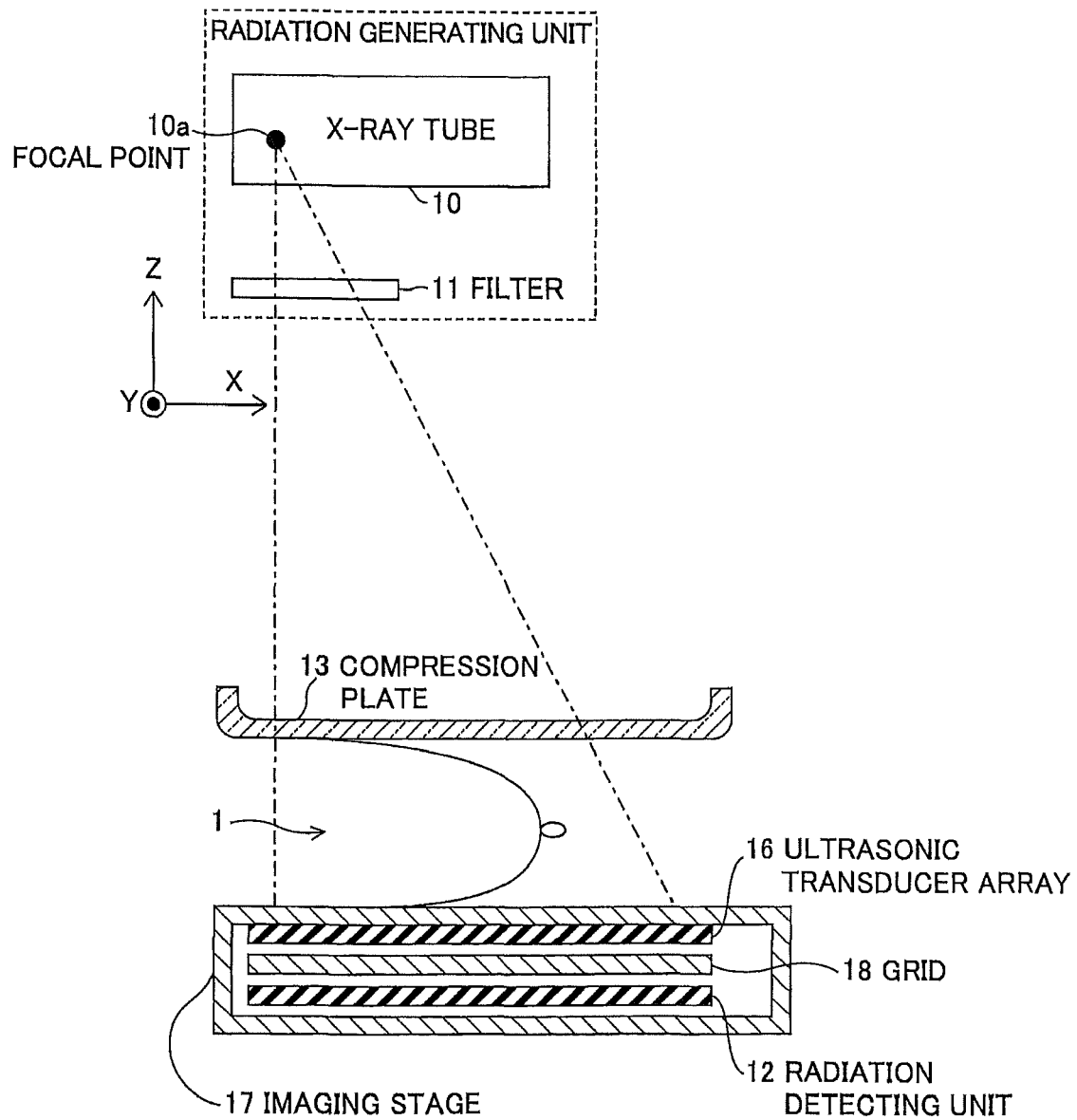
FIG. 3 is an enlarged sectional view showing a part of the imaging unit in the medical imaging apparatus according to the first embodiment of the present invention.

FIG. 3 is an enlarged sectional view showing a part of the imaging unit in the medical imaging apparatus according to the first embodiment of the present invention. The X-ray tube 10 emits an X-ray when a tube voltage is applied thereto. The filter 11 is made of a material such as molybdenum (Mo) or rhodium (Rh), and selectively transmits a desired wavelength component of plural wavelength components included in the X-ray emitted by the X-ray tube 10.

As the radiation detecting unit 12, an imaging plate, flat panel detector (FPD), or the like may be used. In the embodiment, a flat panel detector is used. The flat panel detector detects X-rays at plural points in a two-dimensional area and outputs detection signals (radiation detection signals) having intensity according to X-ray intensity. Further, a grid 18 for preventing scattering of X-rays and improving contrast is provided above the radiation detecting unit 12. The grid 18 includes an X-ray absorbent material such as lead.

The X-ray radiated from the radiation generating unit is transmitted through the compression plate 13, the object 1, the upper part of the imaging stage 17, the ultrasonic transducer array 16, and the grid 18, and then, reaches the radiation detecting unit 12, and a radiation image is formed. The radiation detection signals representing the radiation image are outputted from the radiation detecting unit 12 to the radiation imaging control part 30 (FIG. 1) via a cable.

The ultrasonic transducer array 16 includes two-dimensionally arranged ultrasonic transducers, a wiring pattern for electrically connecting those ultrasonic transducers to the ultrasonic imaging control part 40 (FIG. 1), and a base member for supporting them.

Figure 4A:
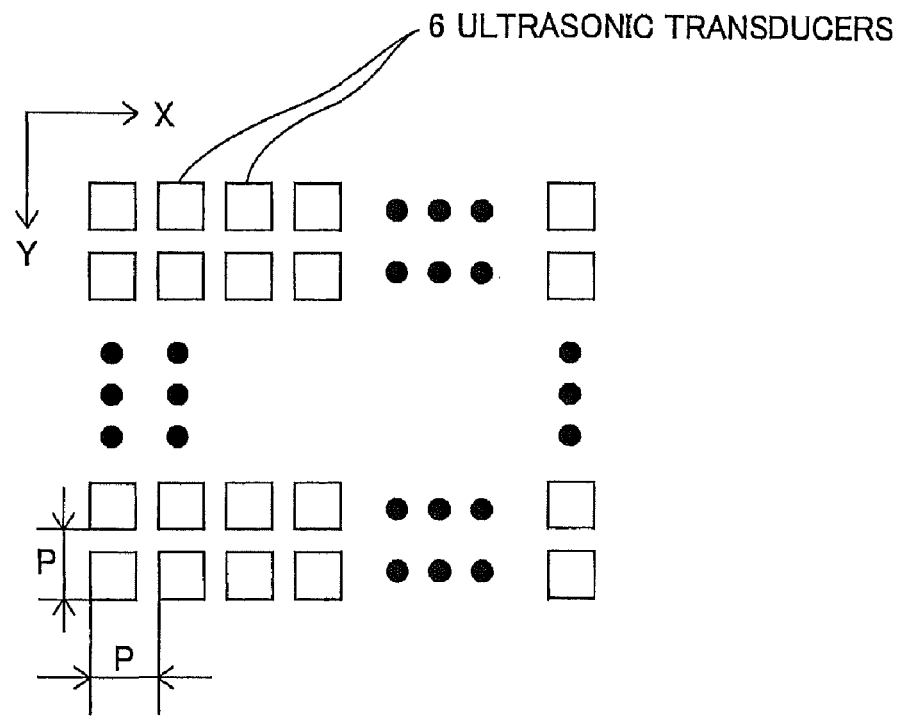
FIG. 4A is a plan view showing an arrangement example of ultrasonic transducers in an ultrasonic transducer array shown in FIG. 3.
Figure 4B:
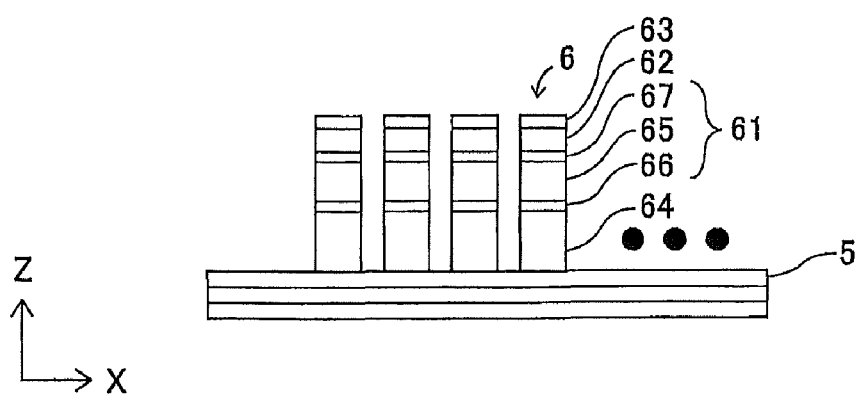
FIG. 4B is a side view showing the arrangement example of the ultrasonic transducers in the ultrasonic transducer array shown in FIG. 3.

FIGS. 4A and 4B are a plan view and a side view showing an arrangement example of the ultrasonic transducers in the ultrasonic transducer array shown in FIG. 3. As shown in FIG. 4A, the plural ultrasonic transducers 6 are arranged in a two-dimensional matrix form with arrangement pitch P along the XY plane. Assuming that the wavelength of ultrasonic waves within a living body is $\lambda$, it is desirable that the value of arrangement pitch P is set to about $\lambda/2$ to $2\lambda$. In breast cancer screening, ultrasonic waves having a frequency of about 10 MHz are generally used, and the arrangement pitch P of the ultrasonic transducers is suitably 0.2 mm to 0.3 mm.

As shown in FIG. 4B, the plural ultrasonic transducers (elements) 6 are mounted on the base member 5. The base member 5 is made of a material including glass epoxy resin, ceramics or silicon, and provided with at least one wiring layer. In the wiring layer, the wiring pattern and a land for mounting elements are formed. Here, the upper surface of the base member 5 may be formed as a curved surface such that the longitudinal direction of the plural ultrasonic transducers 6 may be directed toward the focal point 10a of the X-ray tube (FIGS. 2 and 3).

Each ultrasonic transducer 6 includes a vibrator 61, an acoustic matching layer 62 for providing matching of acoustic impedance between the vibrator and the object (living body) for improvement of propagation efficiency of ultrasonic waves, an acoustic lens (or protective layer) 63 for focusing or diffusing ultrasonic waves, and a backing material 64 for attenuating unwanted ultrasonic waves generated from the vibrator 61.

As the material of the acoustic matching layer 62, for example, a material formed by mixing a material such as epoxy resin, urethane resin, silicon, or acrylic resin and material powder having a high acoustic impedance (tungsten, ferrite powder, or the like) is used. Further, as the material of the backing material 64, epoxy resin, rubber, or the like with great acoustic attenuation is used.

The vibrator 61 includes a material having a piezoelectric property (piezoelectric material 65) such as a piezoelectric ceramic represented by PZT (Pb(lead) zirconate titanate), a polymeric piezoelectric element represented by PVDF (polyvinylidene difluoride), or the like, and an individual electrode 66 and a common electrode 67 formed on ends of the piezoelectric material 65. Generally, the common electrode 67 is connected to the ground potential.

Furthermore, the ultrasonic transducer array may include a filling material filling between the plural vibrators 61 and for reducing interference between the plural vibrators 61 such that the vibrators 61 vibrate only in the longitudinal direction while preventing the lateral vibration. Further, the acoustic matching layer 62 may have a multilayer structure for higher propagation efficiency of ultrasonic waves.

When a pulsed or continuous wave voltage is applied to the electrodes 66 and 67 of the vibrator 61, the piezoelectric material expands and contracts. By the expansion and contraction, pulsed or continuous wave ultrasonic waves are generated from the respective vibrators, and an ultrasonic beam is formed by synthesizing these ultrasonic waves. Further, the respective vibrators expand and contract by receiving propagating ultrasonic waves and generate electric signals. These electric signals are outputted as reception signals.

Referring to FIG. 3 again, in the embodiment, the two-dimensional ultrasonic transducer array 16 is provided within the imaging stage 17, and the ultrasonic transducer array 16 is acoustically connected to the object 1 via the upper part of the imaging stage 17. The ultrasonic waves transmitted from the ultrasonic transducer array 16 according to drive signals supplied from the ultrasonic imaging control part 40 (FIG. 1) via a cable are reflected by the object 1 and generate ultrasonic echoes, and the ultrasonic transducer array 16 receiving the ultrasonic echoes outputs reception signals to the ultrasonic imaging control part 40 via the cable.

According to the embodiment, by using the two-dimensional ultrasonic transducer array 16, it is not necessary to mechanically scan the object 1, and therefore, ultrasonic images can be acquired in a short time. However, the ultrasonic transducer array 16 exists within the X-ray path between the X-ray tube 10 and the radiation detecting unit 12, and in the radiation image, not only the image of the object 1 but also the image of the ultrasonic transducer array 16 (especially, vibrators and wiring pattern) is formed and becomes an obstacle in diagnosis. Accordingly, as specifically described later, image processing is performed for removing the image of the ultrasonic transducer array 16.

Referring to FIG. 1 again, a radiation imaging system will be explained.

The radiation imaging control part 30 includes a tube voltage/tube current control unit 31, a high-voltage generating unit 32, an A/D converter 33, a radiation image data generating unit 34, an image processing unit 35, and an image data storage unit 36.

In the X-ray tube 10, the X-ray transparency is determined according to the tube voltage applied between the cathode and the anode, and the amount of X-ray emission is determined according to the time integration of the tube current flowing between the cathode and the anode (mAs value: tube current time integration). Further, X-ray characteristics are controlled by setting a combination of a target material to be used in the X-ray tube 10 and a material to be used in the filter 11 (e.g., tungsten/rhodium, molybdenum/molybdenum, molybdenum/rhodium, rhodium/rhodium, and so on).

The tube voltage/tube current control unit 31 adjusts imaging conditions of the tube voltage, tube current, and so on according to target values. The target values of the tube voltage and the tube current may be manually adjusted by the operator by using the console 70. The high-voltage generating unit 32 generates a high voltage to be applied to the X-ray tube 10 under the control of the tube voltage/tube current control unit 31.

The A/D converter 33 converts analog radiation detection signals outputted from the radiation detecting unit 12 into digital signals (radiation detection data), and the radiation image data generating unit 34 generates radiation image data based on the radiation detection data.

The image processing unit 35 performs image processing on the radiation image data generated based on the detection results of the radiation generated by the radiation generating unit and transmitted through the object 1 and the ultrasonic transducer array 16, and thereby, removes the image of the ultrasonic transducer array 16 from the radiation image represented by the radiation image data.

In the embodiment, the image processing unit 35 performs subtraction processing between the radiation image including the images of the object 1 and the ultrasonic transducer array 16 and the radiation image of the ultrasonic transducer array 16. For the purpose, radiation imaging of the ultrasonic transducer array 16 is performed when the object 1 does not exist to generate first radiation image data representing the radiation image of the ultrasonic transducer array 16. The generation of the first radiation image data may be performed at any time before factory shipment, at maintenance, or immediately before actual examination. The image processing unit 35 stores the first radiation image data generated by the radiation image data generating unit 34 in the image data storage unit 36.

In the actual examination, radiation imaging of the object 1 is performed to generate second radiation image data based on radiation detection signals obtained by detection of X-rays transmitted through the object 1 and the ultrasonic transducer array 16. The image processing unit 35 performs subtraction processing between the first radiation image data and the second radiation image data to remove the image of the ultrasonic transducer array 16 from the radiation image represented by the second radiation image data.

That is, the image processing unit 35 performs subtraction processing of subtracting values of the first radiation image data from values of the second radiation image data. Since the radiation image varies depending on imaging conditions of tube voltage, tube current time integration, target, filter, and so on used in the radiation generating unit, correction factors are predetermined according to one or a combination of those imaging conditions. The image processing unit 35 corrects the values of the first and/or second radiation image data by using the correction factor determined according to at least one imaging condition, and then, performs the subtraction processing. The image of the grid can be removed in the same manner. When X-ray imaging is performed while the grid is moved, the image of the grid hardly appears.

Figure 5A:
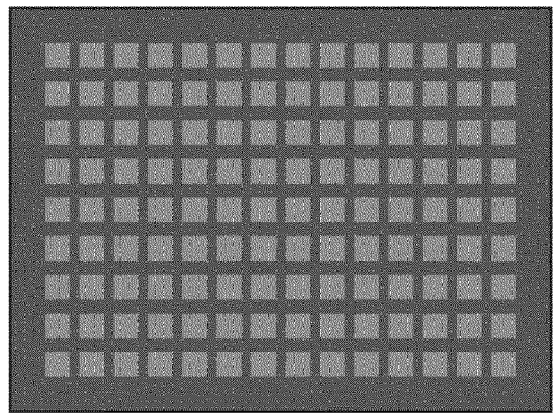
FIG. 5A-5C show radiation images in subtraction processing of the first embodiment.
Figure 5B:
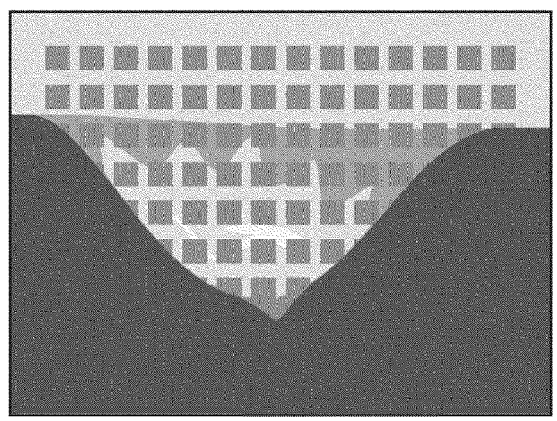
Figure 5C:
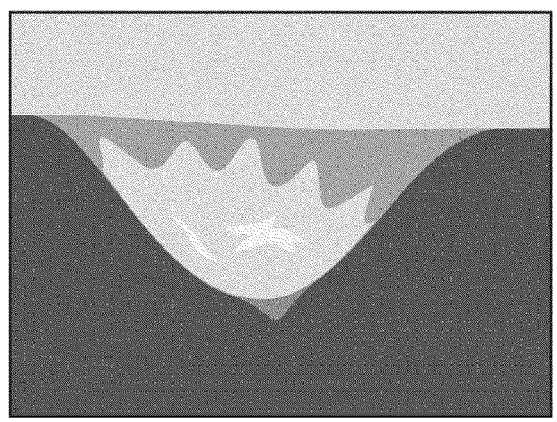

FIG. 5A-5C show radiation images in the subtraction processing of the first embodiment. FIG. 5A shows a radiation image of the ultrasonic transducer array represented by the first radiation image data, FIG. 5B shows a radiation image including the images of the object and the ultrasonic transducer array represented by second radiation image data, and FIG. 5C shows a radiation image of the object represented by subtraction-processed radiation image data.

Next, referring to FIG. 1 again, an ultrasonic imaging system will be explained.

The ultrasonic imaging control part 40 includes a scan control unit 41, a transmission circuit 42, a reception circuit 43, an A/D converter 44, a signal processing unit 45, and a B-mode image data generating unit 46.

The scan control unit 41 sets frequencies and voltages of the drive signals to be applied from the transmission circuit 42 to the respective ultrasonic transducers of the ultrasonic transducer array 16 and adjusts the frequency and sound pressure of the ultrasonic waves to be transmitted under the control of the movement control unit 20. Further, the scan control unit 41 has a transmission control function of transmission directions of ultrasonic beams and selecting transmission delay patterns according to the set transmission directions, and a reception control function of sequentially setting reception directions of ultrasonic echoes and selecting reception delay patterns according to the set reception directions.

Here, the transmission delay pattern refers to a pattern of delay time to be provided to the drive signals for forming an ultrasonic beam in a desired direction with the ultrasonic waves transmitted from the plural ultrasonic transducers of the ultrasonic transducer array 16, and the reception delay pattern refers to a pattern of delay time to be provided to the reception signals for extracting ultrasonic echoes from the desired direction with the ultrasonic waves received by the plural ultrasonic transducers. Plural transmission delay patterns and plural reception delay patterns are stored in a memory or the like.

The transmission circuit 42 generates drive signals to be respectively applied to the plural ultrasonic transducers. In this regard, the transmission circuit 42 may adjust the amounts of delay of the drive signals and supply the drive signals to the ultrasonic transducer array 16 such that the ultrasonic waves to be transmitted from the plural ultrasonic transducers form an ultrasonic beam, or may supply drive signals to the ultrasonic transducer array 16 such that the ultrasonic waves to be transmitted at once from the plural ultrasonic transducers reach the entire imaging region of the object.

The reception circuit 43 amplifies the ultrasonic reception signals respectively outputted from the plural ultrasonic transducers, and the A/D converter 44 converts the analog ultrasonic reception signals amplified by the reception circuit 43 into digital ultrasonic reception signals. The signal processing unit 45 performs reception focus processing by providing the respective delay times to the ultrasonic reception signals based on the reception delay pattern selected by the scan control unit 41, and adding those ultrasonic reception signals to one another. Through the reception focus processing, sound ray signals in which the focal point of the ultrasonic echoes is narrowed is formed.

Furthermore, the signal processing unit 45 corrects attenuation of the sound ray signals by distance according to the depths of the reflection positions of ultrasonic waves through STC (sensitivity time gain control), and then, performs envelope detection processing with a low-pass filter or the like thereon to generate envelope signals.

The B-mode image data generating unit 46 performs processing such as logarithmic compression and gain adjustment on the envelope signals to generate image data, and converts (raster-converts) the image data into image data that follows the normal scan system of television signals to generate B-mode image data.

The image display control unit 50 performs necessary image processing such as gradation process on the radiation image data outputted from the radiation imaging control part 30 and the ultrasonic image data outputted from the ultrasonic imaging control part 40 to generate image data for display and controls display of images. Thereby, radiation images and ultrasonic images are displayed on the display units 51 and 52, respectively.

The console 70 is used by the operator to operate the medical imaging apparatus. The control unit 80 controls the respective parts based on the operation of the operator. So far, the movement control unit 20, the radiation image data generating unit 34, the image processing unit 35, the scan control unit 41, the signal processing unit 45 to the image display control unit 50, and the control unit 80 are configured by a central processing unit (CPU) and software for allowing the CPU to execute various kinds of processing, however, they may be configured by a digital circuit or analog circuit. The software (program) is stored in the storage unit 90 including a hard disk, memory, or the like. Further, the transmission delay patterns and the reception delay patterns to be selected by the scan control unit 41 may be stored in the storage unit 90.

Next, the second embodiment of the present invention will be explained.

Figure 6:
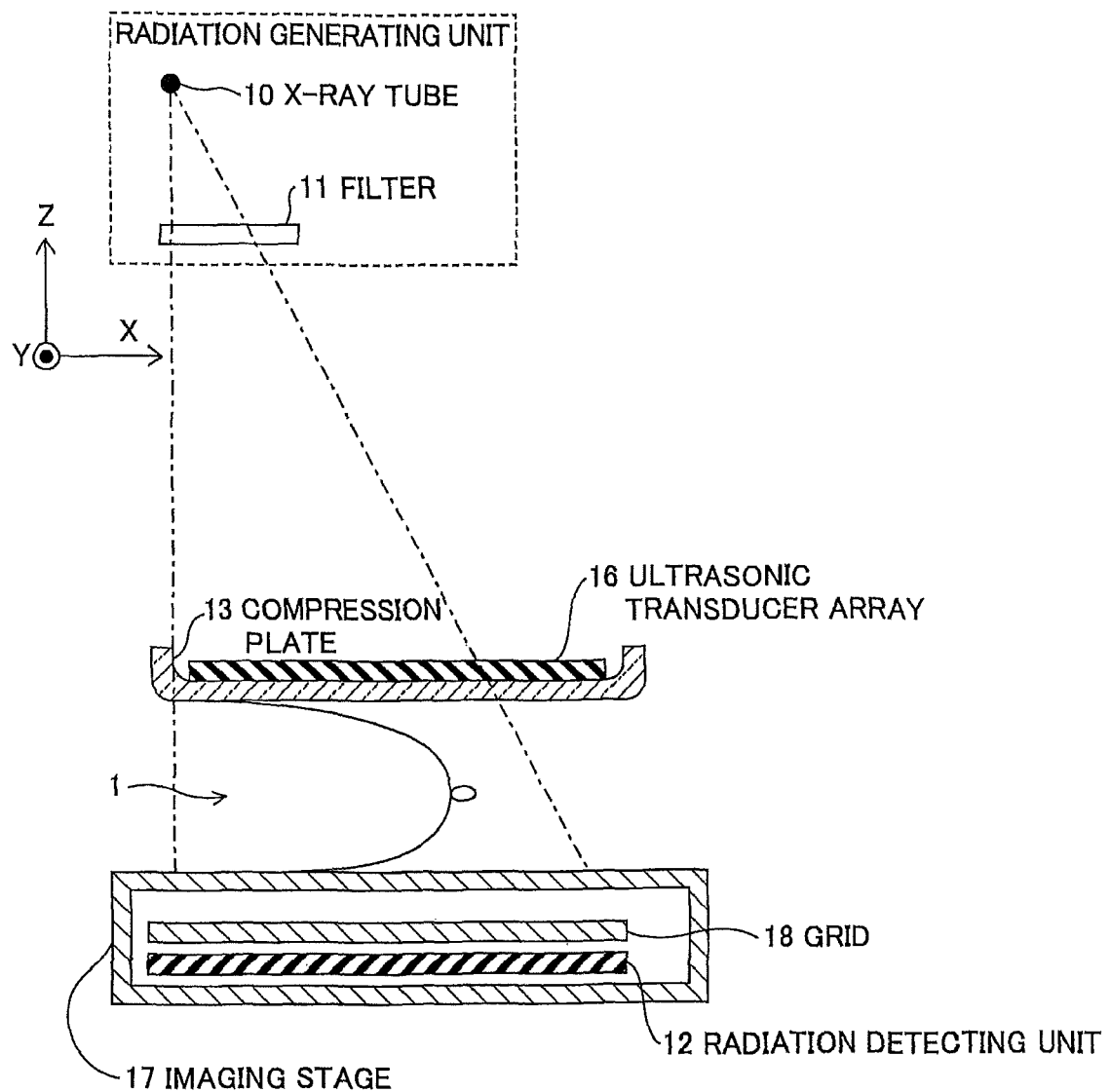
FIG. 6 is an enlarged sectional view showing a part of an imaging unit in a medical imaging apparatus according to the second embodiment of the present invention.

FIG. 6 is an enlarged sectional view showing a part of an imaging unit in a medical imaging apparatus according to the second embodiment of the present invention. The compression plate 13 has a first surface (the lower surface in FIG. 6) for compressing the object 1 along the compression direction (Z-axis direction) and a second surface (the upper surface in FIG. 6) opposite to the first surface. In the second embodiment, the two-dimensional ultrasonic transducer array 16 is provided on the upper surface of the compression plate 13, and the ultrasonic transducer array 16 is acoustically connected to the object 1 via the compression plate 13. The rest of the configuration is the same as that of the first embodiment.

Here, it is desirable that the compression plate 13 is optically transparent for positioning and confirmation of the compression state when compressing the breast, and formed of a material that transmits the X-ray radiated from the X-ray tube 10 and easily propagates ultrasonic waves transmitted from the ultrasonic transducer array 16. As the material of the compression plate 13, for example, a resin such as polycarbonate, acryl, or polymethylpentene having suitable values in acoustic impedance that has influence on reflectance of ultrasonic waves and attenuation factor that has influence on attenuation of ultrasonic waves may be used.

The X-ray radiated from the radiation generating unit is transmitted through the ultrasonic transducer array 16, the compression plate 13, the object 1, the upper part of the imaging stage 17, and the grid 18, and then, reaches the radiation detecting unit 12, and a radiation image is formed. According to the second embodiment, since the X-ray radiated from the radiation generating unit is transmitted through the ultrasonic transducer array 16 before applied to the object 1, in the case where the same X-ray intensity as that in the first embodiment is obtained in the radiation detecting unit 12, the amount of X-ray exposure of the object 1 can be reduced. However, the distance between the compression plate 13 and the radiation detecting unit 12 changes due to the thickness of the object 1, and the scaling factor of the image of the two-dimensional ultrasonic transducer array 16 provided on the upper surface of the compression plate 13 also changes according to the thickness.

Accordingly, the image processing unit 35 shown in FIG. 1 receives information on a position in the compression direction (Z-axis direction) of the compression plate 13 from the movement control unit 20, and calculates the scaling factor of the image of the ultrasonic transducer array 16 based on the information. For example, by setting the scaling factor when the compression plate 13 contacts the imaging stage 17 in the lowermost position to "1" and performing radiation imaging of the ultrasonic transducer array 16, the first radiation image data representing the radiation image of the ultrasonic transducer array 16 is generated. The image processing unit 35 stores the first radiation image data generated by the radiation image data generating unit 34 in the image data storage unit 36.

In the actual examination, the image processing unit 35 calculates scaling factor α when the compression plate 13 contacts the object 1. Concurrently, by performing radiation imaging of the object 1, the second radiation image data is generated based on radiation detection signals obtained by detection of X-rays transmitted through the ultrasonic transducer array 16 and the object 1. The image processing unit 35 processes the first radiation image data to enlarge the image of the ultrasonic transducer array 16 represented by the first radiation image data according to the calculated scaling factor α, and performs subtraction processing between the second radiation image data and the first radiation image data to remove the image of the ultrasonic transducer array 16 from the radiation image represented by the second radiation image data.

The case where α<1 may occur depending on the position of the compression plate 13 when the first radiation image data is acquired. In this case, the image processing unit 35 processes the first radiation image data to reduce the image of the ultrasonic transducer array 16 represented by the first radiation image data according to the calculated scaling factor α. Also in the embodiment, the image processing unit 35 may correct the values of the first and/or second radiation image data by using the correction factor determined according to at least one of imaging conditions of tube voltage, tube current time integration, target, filter, and so on used in the radiation generating unit, and then, perform the subtraction processing.

Figure 7A:
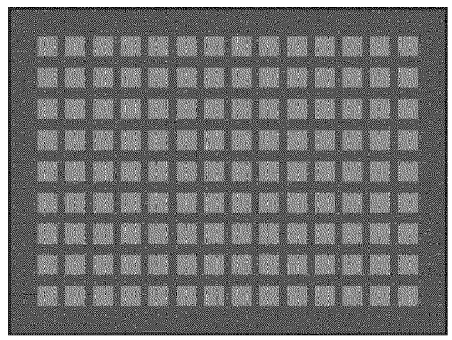
FIG. 7A-7D show radiation images in subtraction processing of the second embodiment.
Figure 7B:
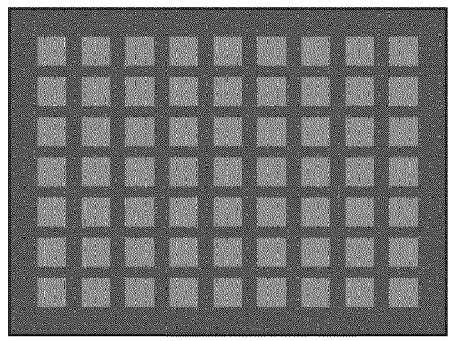
Figure 7C:
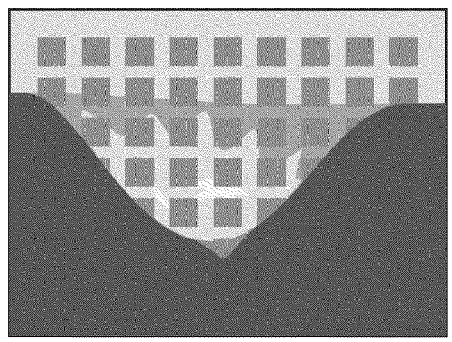
Figure 7D:
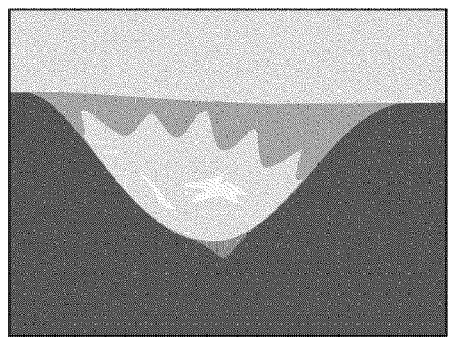

FIG. 7A-7D shows radiation images in the subtraction processing of the second embodiment. FIG. 7A shows a radiation image of the ultrasonic transducer array represented by the first radiation image data, FIG. 7B shows an enlarged radiation image of the ultrasonic transducer array, FIG. 7C shows a radiation image of the object and the ultrasonic transducer array represented by second radiation image data, and FIG. 7D shows a radiation image of the object represented by subtraction-processed radiation image data.

Next, the third embodiment of the present invention will be explained. In the third embodiment, instead of the subtraction processing, filtering processing is performed on the radiation images. The rest of the configuration is the same as that of the first or second embodiment.

As shown in FIG. 4A, the plural ultrasonic transducers 6 are arranged in a two-dimensional matrix form with arrangement pitch P along the XY plane, and the radiation image including the image of the ultrasonic transducer array includes specific spatial frequency components due to the arrangement pitch P. Accordingly, the image processing unit 35 shown in FIG. 1 calculates spatial frequency data by two-dimensional Fourier transform of the radiation image data generated based on the detection results of the X-rays transmitted through the object 1 and the ultrasonic transducer array 16.

Figure 8A:
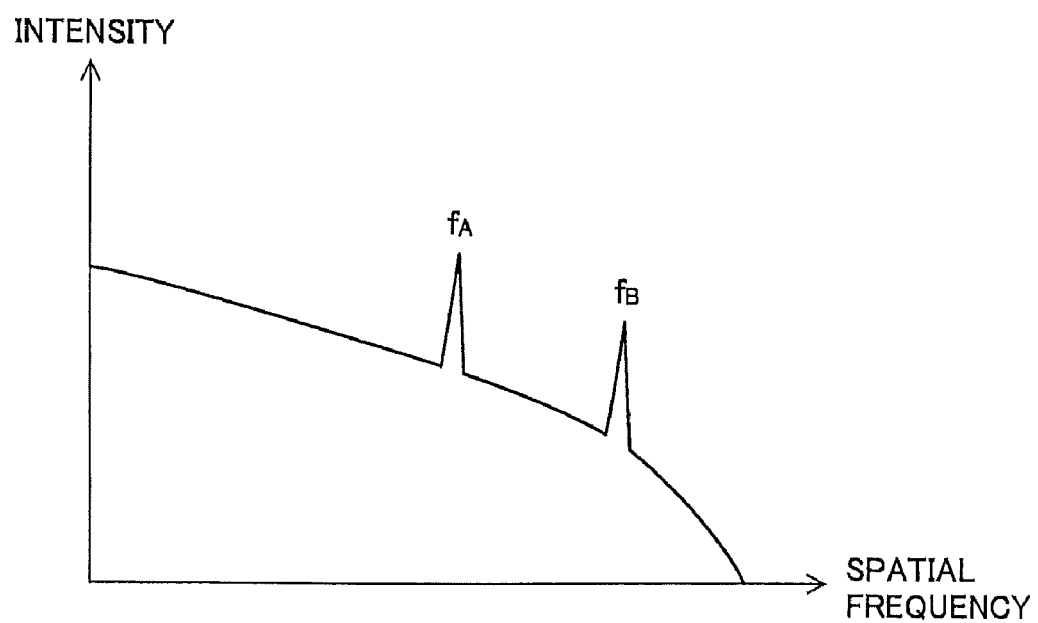
FIG. 8A shows a spatial frequency spectrum represented by spatial frequency data of a radiation image including an image of the ultrasonic transducer array.

FIG. 8A shows a spatial frequency spectrum represented by the spatial frequency data of the radiation image including the image of the ultrasonic transducer array. The spatial frequency spectrum includes specific spatial frequency component $f_A$ due to the arrangement pitch of the ultrasonic transducer array and specific spatial frequency component $f_B$ due to the arrangement pitch of the grid. Accordingly, the image processing unit 35 removes at least the specific spatial frequency component $f_A$ corresponding to the arrangement pitch of the ultrasonic transducer array, and interpolates the part based on the other spatial frequency components in the spatial frequency data. Furthermore, the image processing unit 35 may remove the specific spatial frequency component $f_B$ corresponding to the arrangement pitch of the grid, and interpolate the part based on the other spatial frequency components in the spatial frequency data. When X-ray imaging is performed while the grid is moved, the specific spatial frequency component $f_B$ due to the arrangement pitch of the grid hardly appears.

Figure 8B:
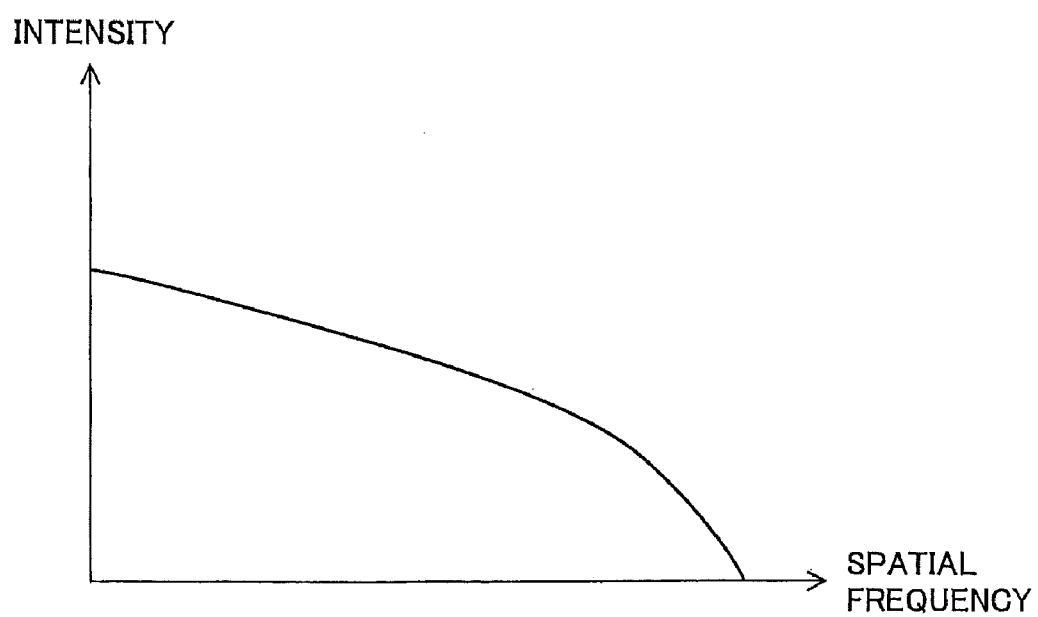
FIG. 8B shows a spatial frequency spectrum represented by spatial frequency data in which a specific spatial frequency component corresponding to an arrangement pitch of the ultrasonic transducer array has been removed.

FIG. 8B shows a spatial frequency spectrum represented by the spatial frequency data in which the specific spatial frequency component $f_A$ corresponding to the arrangement pitch of the ultrasonic transducer array has been removed. Then, the image processing unit 35 calculates radiation image data by inverse two-dimensional Fourier transform of the spatial frequency data. In the radiation image data, the image of the ultrasonic transducer array has been removed.

The invention claimed is:

1. A medical imaging apparatus comprising:
   a radiation generating unit for generation radiation;
   a radiation detecting unit for detecting radiation;
   an ultrasonic transducer array provided between said radiation generating unit and said radiation detecting unit, said ultrasonic transducer array including two-dimensionally arranged ultrasonic transducers;
   a radiation image data generating unit for generating radiation image data based on a detection result of said radiation detecting unit; and
   an image processing unit for performing image processing on the radiation image data generated based on a detection result of radiation generated by said radiation generating unit and transmitted through an object to be inspected and said ultrasonic transducer array, thereby removing an image of said ultrasonic transducer array from a radiation image represented by the radiation image data.

2. The medical imaging apparatus according to claim 1, further comprising:
an imaging stage on which the object is mounted; and
a compression plate having a first surface for compressing the object and a second surface opposed to the first surface, for compressing the object between said imaging stage and itself,
wherein said ultrasonic transducer array is provided within said imaging stage.

3. The medical imaging apparatus according to claim 1, further comprising:
an imaging stage on which the object is mounted; and
a compression plate having a first surface for compressing the object and a second surface opposed to the first surface, for compressing the object between said imaging stage and itself,
wherein said ultrasonic transducer array is provided on the second surface of said compression plate.

4. The medical imaging apparatus according to claim 2, further comprising:
a storage unit for storing first radiation image data representing a radiation image of said ultrasonic transducer array,
wherein said image processing unit performs subtraction processing of subtracting values of the first radiation image data from values of second radiation image data generated based on the detection result of the radiation generated by said radiation generating unit and transmitted through the object and said ultrasonic transducer array.

5. The medical imaging apparatus according to claim 3, further comprising:
a storage unit for storing first radiation image data representing a radiation image of said ultrasonic transducer array,
wherein said image processing unit calculates a scaling factor of an image of said ultrasonic transducer array based on information on a position of said compression plate in a compression direction, processes the first radiation image data to enlarge or reduce the radiation image according to the calculated scaling factor, and performs subtraction processing of subtracting values of the first radiation image data from values of second radiation image data generated based on the detection result of the radiation generated by said radiation generating unit and transmitted through the object and said ultrasonic transducer array.

6. The medical imaging apparatus according to claim 4, wherein said image processing unit corrects the values of the first and/or second radiation image data by using a correction factor determined according to at least one of imaging conditions of tube voltage, tube current time integration, target, and filter used in said radiation generating unit, and performs the subtraction processing.

7. The medical imaging apparatus according to claim 5, wherein said image processing unit corrects the values of the first and/or second radiation image data by using a correction factor determined according to at least one of imaging conditions of tube voltage, tube current time integration, target, and filter used in said radiation generating unit, and then, performs the subtraction processing.

8. The medical imaging apparatus according to claim 1, wherein said image processing unit calculates spatial frequency data by two-dimensional Fourier transform of the radiation image data generated based on the detection result of the radiation generated by said radiation generating unit and transmitted through the object and said ultrasonic transducer array, removes at least a specific spatial frequency component corresponding to an arrangement pitch of said ultrasonic transducer array in the spatial frequency data, and performs inverse two-dimensional Fourier transform of the spatial frequency data, thereby calculates radiation image data in which the image of said ultrasonic transducer array has been removed.

* * * * *